United States Patent
Sattler et al.

(10) Patent No.: US 10,791,956 B2
(45) Date of Patent: Oct. 6, 2020

(54) DEVICE FOR AN IMPEDANCE TOMOGRAPH

(71) Applicant: Drägerwerk AG & Co. KGaA, Lübeck (DE)

(72) Inventors: Frank Sattler, Lübeck (DE); Karsten Hiltawsky, Stockelsdorf (DE); Jian-Hua Li, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 332 days.

(21) Appl. No.: 15/323,571

(22) PCT Filed: Jul. 1, 2015

(86) PCT No.: PCT/EP2015/001320
§ 371 (c)(1),
(2) Date: Jan. 3, 2017

(87) PCT Pub. No.: WO2016/000821
PCT Pub. Date: Jan. 7, 2016

(65) Prior Publication Data
US 2017/0135601 A1    May 18, 2017

(30) Foreign Application Priority Data
Jul. 4, 2014    (DE) .................. 10 2014 009 890

(51) Int. Cl.
*A61B 5/00*    (2006.01)
*A61B 5/053*    (2006.01)
*A61N 1/39*    (2006.01)

(52) U.S. Cl.
CPC .......... *A61B 5/0536* (2013.01); *A61N 1/3931* (2013.01); *A61B 2562/043* (2013.01); *A61B 2562/18* (2013.01)

(58) Field of Classification Search
CPC ..................... A61B 5/0536; A61N 1/3931
See application file for complete search history.

(56) References Cited

U.S. PATENT DOCUMENTS 3,910,257 A * 10/1975 Fletcher ............... A61B 5/0006
128/908
4,041,954 A * 8/1977 Ohara ................... A61N 1/3787
128/908
(Continued)

FOREIGN PATENT DOCUMENTS

| CN | 1795815 A | 7/2006 |
|---|---|---|
| DE | 10 2005 041 385 A1 | 3/2007 |
| EP | 1 676 528 A1 | 7/2006 |

OTHER PUBLICATIONS

Kim, "A flexible capacitor based on conducting polymer electrodes", Synthetic Metals, 161, 1130-1132 (Year: 2011).*
(Continued)

*Primary Examiner* — Joanne M Hoffman
(74) *Attorney, Agent, or Firm* — McGlew and Tuttle, P.C.

(57) ABSTRACT

A device (2) for an electrical impedance tomograph (3) includes an electrode carrier (4), first and second skin electrodes (6, 8), which are arranged on the electrode carrier (4) at mutually spaced locations from one another in the longitudinal direction (L) of the electrode carrier, as well as a first protective circuit (10), which is at least partly enclosed in the electrode carrier (4). A second protective circuit (12) is provided, which is at least partly enclosed in the electrode carrier (4). The first protective circuit (10) is electrically connected to the first skin electrode (6), and the second protective circuit (12) is electrically connected to the second skin electrode (8).

11 Claims, 2 Drawing Sheets

(56) References Cited

U.S. PATENT DOCUMENTS

| | | | | |
|---|---|---|---|---|
| 4,419,998 | A * | 12/1983 | Heath | A61B 18/16 600/391 |
| 4,660,568 | A * | 4/1987 | Cosman | A61B 5/0002 600/561 |
| 4,744,369 | A * | 5/1988 | Kroll | H02H 9/025 128/908 |
| 4,850,356 | A * | 7/1989 | Heath | A61B 18/16 607/142 |
| 4,974,600 | A * | 12/1990 | Reyes | A61B 5/04286 600/509 |
| 5,080,099 | A * | 1/1992 | Way | A61B 5/0408 600/391 |
| 5,295,482 | A * | 3/1994 | Clare | A61N 1/0492 600/385 |
| 5,782,241 | A * | 7/1998 | Felblinger | A61B 5/02438 128/908 |
| 5,792,185 | A * | 8/1998 | Burton | A61N 1/3931 607/2 |
| 5,916,244 | A * | 6/1999 | Walters | A61N 1/0492 607/142 |
| 6,148,233 | A * | 11/2000 | Owen | A61N 1/0452 607/5 |
| 6,373,395 | B1 * | 4/2002 | Kimsey | A61F 13/42 340/573.5 |
| 6,405,083 | B1 * | 6/2002 | Rockwell | A61N 1/39 128/903 |
| 6,658,291 | B2 * | 12/2003 | Snyder | A61B 5/04087 607/142 |
| 6,711,434 | B2 * | 3/2004 | Kramer | A61B 5/0428 600/509 |
| 6,714,824 | B1 * | 3/2004 | Ohta | A61N 1/046 607/142 |
| 7,680,523 | B2 | 3/2010 | Rytky | |
| 7,822,488 | B2 * | 10/2010 | Jonsen | A61N 1/046 206/701 |
| 8,050,733 | B2 | 11/2011 | Rytky | |
| 9,384,549 | B2 * | 7/2016 | Leonhardt | G06T 7/0016 |
| 10,070,798 | B2 * | 9/2018 | Korkala | A61B 5/0408 |
| 2002/0079910 | A1 * | 6/2002 | Fukuda | A61B 5/05 324/692 |
| 2004/0121528 | A1 * | 6/2004 | Krulevitch | A61N 1/0452 438/166 |
| 2006/0022882 | A1 * | 2/2006 | Gerder | H01Q 1/273 343/718 |
| 2006/0058600 | A1 * | 3/2006 | Eichler | A61B 5/0536 600/407 |
| 2007/0049993 | A1 * | 3/2007 | Hofmann | A61B 5/0536 607/62 |
| 2010/0274327 | A1 * | 10/2010 | Carroll | A61N 1/0456 607/72 |
| 2011/0152644 | A1 * | 6/2011 | Heck | A61B 5/14532 600/309 |
| 2013/0041235 | A1 * | 2/2013 | Rogers | A61B 5/1107 600/306 |
| 2013/0345535 | A1 * | 12/2013 | Elschenbroich | A61B 5/04282 600/372 |
| 2014/0213883 | A1 * | 7/2014 | Banet | A61B 5/6802 600/395 |
| 2014/0316230 | A1 * | 10/2014 | Denison | A61B 5/04012 600/383 |
| 2014/0324120 | A1 * | 10/2014 | Bogie | A61N 1/0468 607/46 |
| 2015/0335877 | A1 * | 11/2015 | Jeffery | A61N 1/0492 607/139 |
| 2017/0056682 | A1 * | 3/2017 | Kumar | A61N 1/3968 |
| 2017/0156631 | A1 * | 6/2017 | Sattler | H01R 13/6666 |

OTHER PUBLICATIONS

DE-202005013792-U1, Derwint (Year: 2005).*

Chang-Ming Yang et al: "Performance assessment of active electrode applied in wearable physiological monitoring system", Biomedical and Health Informatics (BH I), 2012 IEEE-EMBS International Conference on, IEEE, Jan. 5, 2012 (Jan. 5, 2012), pp. 472-474.

* cited by examiner

US 10,791,956 B2

DEVICE FOR AN IMPEDANCE TOMOGRAPH

CROSS REFERENCE TO RELATED APPLICATIONS

This application is a United States National Phase Application of International Application PCT/EP2015/001320 filed Jul. 1, 2015, and claims the benefit of priority under 35 U.S.C. § 119 of German Application 10 2014 009 890.7 filed Jul. 4, 2014, the entire contents of which are incorporated herein by reference.

FIELD OF THE INVENTION

The present invention pertains to a device for an electrical impedance tomograph with an electrode carrier, with a first skin electrode and with a second skin electrode, which are arranged on the electrode carrier at mutually spaced locations from one another in the longitudinal direction of the electrode carrier, as well as with a first protective circuit, which is enclosed at least partly in the electrode carrier.

BACKGROUND OF THE INVENTION

Electrodiagnostic methods are frequently used on patients who are in a critical condition. It may become necessary now to use a defibrillator for a short time, without there being enough time to properly disconnect diagnostic devices from the patient. This leads to the risk of damage to the diagnostic devices due to overvoltage pulses.

Defibrillation is the only effective and life-saving procedure in life-threatening situations, such as ventricular fibrillation or pulseless ventricular tachycardia.

Any delay that would arise from the arise of electrodes or electric terminals from the patient is to be avoided.

Input resistances in the range or 10 kohms to 50 kohms are used according to the state of the art in pure ECG devices or in combined ECG/impedance-measuring devices that are not used for imaging methods in order to prevent technical damage due to the use of defibrillators.

The special difficulty in impedance-tomographic methods is that, unlike in pure electrocardiography, the electrodes are often provided for a dual purpose in applications in thoracic electrical impedance tomography.

First, they shall introduce into the patient the stimulating currents, which may reach up to 10 mA and with which a readily analyzable potential distribution shall be achieved in the patient.

Second, they shall feed the low signal voltages, which are measured on the skin surface of the patient based on the potential distribution generated with the stimulating currents, to the input amplifier or to an analysis unit. The signal voltages to be measured may be in the μV to mV range.

The currents to be introduced must be selected at high values, up to 10 mA, in order to generate sufficient potential differences in the entire thorax in order to be able to generate an image from the potentials picked off. Voltages of 100 V to 500 V would drop over resistances of 10 kohms to 50 kohms. Such voltages cannot be used on the patient, and the possibility of protecting the impedance tomograph by sufficiently high protective resistors cannot be taken into consideration.

Protecting the inputs by varistors or diodes connected in parallel to the input amplifier is likewise problematic. Additional stray capacitances, which are connected between the signal line and the reference potential, must be kept as low as possible. This is necessary to prevent unacceptable reactive impedances, which are located parallel to the input of the first amplifier stage, from developing at the usual operating frequencies of about 10 kHz to 200 kHz. They would unacceptably increase the load, which the measuring circuit represents against the potential distribution on the skin surface of the patient and thus they would distort the measurement. At a frequency of 50 kHz, 10 pF already represents an impedance of about 30 kohms. Thus, solutions that contain varistors or diodes connected in parallel to the input amplifier are disadvantageous if the parasitic capacitance of these varistors or diodes is higher than a few pF. However, this rules out all types that could dissipate the currents that usually develop due to a defibrillator shock.

It must therefore be assumed that the defibrillator is used without the patient being disconnected from the impedance tomograph. In addition to the necessary protection of the impedance tomograph from an overload, it becomes necessary to avoid an excessive draining of the energy of the defibrillator pulse in order not to unacceptably limit the efficiency of the defibrillator.

For example, standards require that a maximum of 10% of the energy of a defibrillator pulse may be dissipated by the measuring circuit if the effectiveness shall be assumed to be still sufficient.

Equivalent standard specifications for thoracic impedance tomographs can undoubtedly be expected in case this diagnostic method becomes established. While components of the device that are possibly at risk must be protected, effective use of the defibrillator for the protection of the patient must be guaranteed.

Therefore, there was a requirement to provide a device that offers reliable protection against damage caused by overvoltage for an electrical impedance tomograph connected to a patient in case of application of a defibrillator, without the risk of draining of the defibrillator pulses to an extent that is disadvantageous for the effectiveness of defibrillation, and the impedance tomograph shall continue to be able to function at the same time.

A device for protecting an electrical impedance tomograph, which meets the above-mentioned requirement, is known, for example, from the document DE 10 2005 041 385 A1. It discloses an electrical impedance tomograph, whose signal inputs are provided with a protective circuit, which protects the signal inputs against excessively high input currents when a voltage that is excessively high for the normal measuring operation, the protective circuit being integrated in an electrode carrier used with the impedance tomograph.

Electrode carriers with a plurality of skin electrodes, which are arranged on the electrode carrier at mutually spaced locations from one another in a longitudinal direction of the electrode carrier, are usually used in practice. For example, at least two, three, five, ten, fifteen or more skin electrodes may thus be provided. If the device used in the above-mentioned document is now used to protect the electrical impedance tomograph, all skin electrodes are first to be connected electrically to the protective circuit in order to reliably protect the electrical impedance tomograph arranged downstream in the signal conduction direction against damages caused by overvoltage. The electrical connections between the protective circuit preferably integrated in the electrode carrier and the plurality of skin electrodes are each shielded specially electrically in order to prevent the user from being inadvertently exposed to the above-mentioned high voltages of about 100 V to 500 V. In other words, the skin electrodes are to be connected by specially configured electrical line connections to the one protective circuit integrated in the electrode carrier in a Y-shaped manner.

It was found in the case of the aforementioned Y-shaped type of connection that corresponding electrical lines can often be manufactured in a very complicated manner and are therefore very expensive, because, in addition to the protection to be provided, such connections also must offer high flexibility in order for the electrode carrier to be able to be placed on the patient's body without a gap to the extent possible.

SUMMARY OF THE INVENTION

A basic object of the present invention is therefore to provide a flexible device that can be manufactured as cost-effectively as possible for an electrical impedance tomograph with an electrode carrier and with a plurality of skin electrodes, which reliably protects a connected electrical impedance tomograph in case of the use of a defibrillator.

Provided for this is a device for an electrical impedance tomograph with an electrode carrier; with a first skin electrode and with a second skin electrode, which are arranged on the electrode carrier at mutually spaced locations from one another in the longitudinal direction of the electrode carrier; as well as with a first protective circuit, which is enclosed at least partly in the electrode carrier, wherein the device has a second protective circuit, which is enclosed at least partly in the electrode carrier; the first protective circuit being electrically connected to the first electrode and the second protective circuit being electrically connected to the second electrode.

The present invention is based on the discovery that a central protective circuit occupies a comparatively large space, so that if such a protective circuit is integrated in the electrode carrier, the latter will lose its necessary flexibility to be able to be placed on the body of a patient without gaps. In addition, the electrical connection lines in prior-art devices have a Y-shaped configuration in relation to the plurality of electrodes. These connection lines must be both flexible and configured in an electrically shielding and protected manner. Such electrical connection lines can be manufactured at a very high cost only. The basic idea of the present invention is therefore to provide a plurality of protective circuits, especially two protective circuits, which are connected to different skin electrodes each. It can thus be guaranteed that the protective circuits can be arranged close to the electrodes. The electrical connections between the protective circuit and the respective, at least one corresponding skin electrode can be configured as very short connection. The length of the connection lines as well as the manufacturing costs will thus decrease. In addition, a smaller number of skin electrodes is associated with the protective circuits according to the present invention, so that the protective circuits have a significantly smaller type of construction. They can therefore be integrated in the electrode carrier without the latter losing its necessary flexibility.

According to the embodiment according to the present invention, at least two protective circuits are provided which are each enclosed in the electrode carrier. In addition, each of the protective circuits is electrically connected to at least one corresponding skin electrode. Each of the protective circuits is especially preferably arranged adjacent to its corresponding skin electrode. This guarantees the especially short distance between the respective protective circuit and the corresponding skin electrode.

A preferred embodiment of the device is characterized in that the first protective circuit comprises a first capacitor and the second protective circuit comprises a second capacitor. The capacitor called the second capacitor does not assume that the second protective circuit has two or more capacitors. It may rather be only the second capacitor. Each of the protective circuits thus has a separate capacitor. The capacitors can thus be adapted to the corresponding requirements. In addition, each of the capacitors has a relatively small overall size, so that the necessary flexibility of the electrode carrier is guaranteed.

Another advantageous embodiment of the device is characterized in that one of the protective circuits is arranged between the first skin electrode and the second skin electrode in the longitudinal direction. The first skin electrode and the second skin electrode are arranged according to the present invention on the electrode carrier. This shall also cover the case in which the skin electrodes are enclosed at least partly in the electrode carrier. If a protective circuit were arranged only above a corresponding skin electrode, the thickness of the electrode carrier would increase, as a rule, at least in this area. Due to at least one of the protective circuits being arranged between the first skin electrode and the second skin electrode in the longitudinal direction, the undesired effect of an increased thickness of the electrode carrier can be avoided. It is rather possible with this embodiment variant to keep the thickness of the electrode carrier as small as possible. This guarantees, moreover, good flexibility. Both the first protective circuit and the second protective circuit are especially preferably arranged each between two skin electrodes. The electrode carrier can thus have the smallest possible thickness when viewed in the longitudinal direction.

Another advantageous embodiment of the present invention is characterized in that one of the protective circuits and one of the skin electrodes overlap in the longitudinal direction. This embodiment is especially advantageous if the protective circuit has an area with a small thickness and an area with a greater thickness. The protective circuit can be arranged in this case between two skin electrodes with its area of greater thickness and above one of the abovementioned skin electrodes with its area having the reduced thickness. The protective circuit overlaps one of the electrodes in the longitudinal direction in this case and nevertheless guarantees that the electrode carrier can be configured with the smallest possible thickness. Moreover, it may happen that the skin electrodes are arranged so closely adjacent to one another that the protective circuit cannot be arranged between the electrodes. It is useful in this case to enclose the at least one protective circuit in the electrode carrier such that it overlaps one of the skin electrodes in the longitudinal direction. If the protective circuit is connected to a plurality of skin electrodes, provisions may also be made for the protective circuit to overlap a plurality of skin electrodes.

Another advantageous embodiment of the device is characterized in that the first protective circuit and the second protective circuit comprise an interface each to a control unit. The control unit may be configured for preprocessing data and/or for controlling the currents to be introduced by means of the impedance tomograph. Such a control unit preferably comprises active components, which are to be protected from an increased voltage as can be delivered by a defibrillator. Due to the protective circuits being located between the skin electrodes and the control unit, the control unit is protected by the protective circuits. The control unit may preferably be an integral component of the impedance tomograph. As an alternative, provisions may be made for the control unit to be fastened to the electrode carrier and/or to be arranged on same. Such a control unit is especially preferably arranged on an end section of the electrode carrier in order to continue to guarantee the flexibility of the electrode carrier in the area of the electrodes.

Another preferred embodiment of the device is characterized in that the first skin electrode and the second skin electrode are detachably fastened to the electrode carrier. The electrode carrier and the skin electrodes can thus be cleaned and/or reprocessed separately after use. In addition, the separate configuration offers the possibility of replacing a defective skin electrode or a defective electrode carrier and to retain the other parts.

Another advantageous embodiment is characterized in that the first skin electrode and the second skin electrode are integrated in the electrode carrier. This embodiment ensures that a connection between the protective circuit and the corresponding skin electrode is not inadvertently accessible. The skin electrode and the protective circuit are rather preferably encapsulated by the electrode carrier. This offers an especially reliable protection for the user and/or the patient.

Another advantageous embodiment of the device is characterized in that the at least one capacitor is configured as an SMD. SMD means a surface mount device. The capacitor can thus be arranged directly on a board of the corresponding protective circuit, which makes an especially small type of construction possible for the corresponding protective circuit. This protective circuit can therefore be arranged between two skin electrodes or overlapping with a corresponding skin electrode. Moreover, the necessary flexibility of the electrode carrier can be guaranteed with the small space needed for the installation of the protective circuit.

Another advantageous embodiment of the device is characterized in that the at least one capacitor is configured as a flexible capacitor. The first capacitor and/or the second capacitor an thus be configured each as a flexible capacitor. If the at least capacitor is enclosed in the electrode carrier or is surrounded by same, the electrode carrier continues to be flexible. The electrode carrier with the skin electrodes arranged on it can therefore be placed on the body of a patient especially flexibly and adaptably.

Another advantageous embodiment of the device is characterized in that a dielectric of the at least one capacitor is configured as a flexible foil. If the capacitor has, moreover, for example, metallic capacitor electrodes, which have a corresponding flexibility, the corresponding capacitor as such also has a flexible configuration. Such a capacitor therefore has the advantages as explained in connection with the previous, preferred embodiment of the device. Reference is therefore made to the corresponding details and advantages.

Another advantageous embodiment of the device is characterized in that the capacitor electrodes of each capacitor are configured as a flexible foil. The capacitor can thus be inserted into the electrode carrier in an especially simple manner. In addition, the capacitor is configured as a whole as a flexible capacitor with flexible foils as capacitor electrodes and with an additional flexible foil as a dielectric, and this flexible capacitor can, moreover, be enclosed or integrated in the electrode carrier in an especially simple manner.

Another advantageous embodiment of the device is characterized in that at least one part of the electrode carrier is formed by the at least one capacitor. Even if the electrode carrier is preferably configured as a flexible electrode carrier, a certain strength proved to be advantageous in practice. If the electrode carrier is formed at least partly by the capacitor, the capacitor electrodes can, for example, co-determine the desired flexural strength and/or tensile strength of the electrode carrier.

Another advantageous embodiment of the device is characterized in that the electrode carrier forms at least one part of a dielectric of the at least one capacitor. The first capacitor and/or the second capacitor can thus be manufactured in a common process step for manufacturing the electrode carrier. This offers, moreover, the advantage that the at least one capacitor is not accessible to the user from the outside, but is correspondingly shielded. Such an electrode carrier is therefore especially protected. In addition, such an integration of a capacitor in the electrode carrier is especially compact.

Further advantageous features of the present invention appear from the description of the embodiments according to the present invention together with the claims and/or the attached drawings. Embodiments according to the present invention may accomplish individual features or a combination of a plurality of features. The present invention will be described below without limitation of the general inventive idea on the basis of exemplary embodiments with reference to the drawings.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
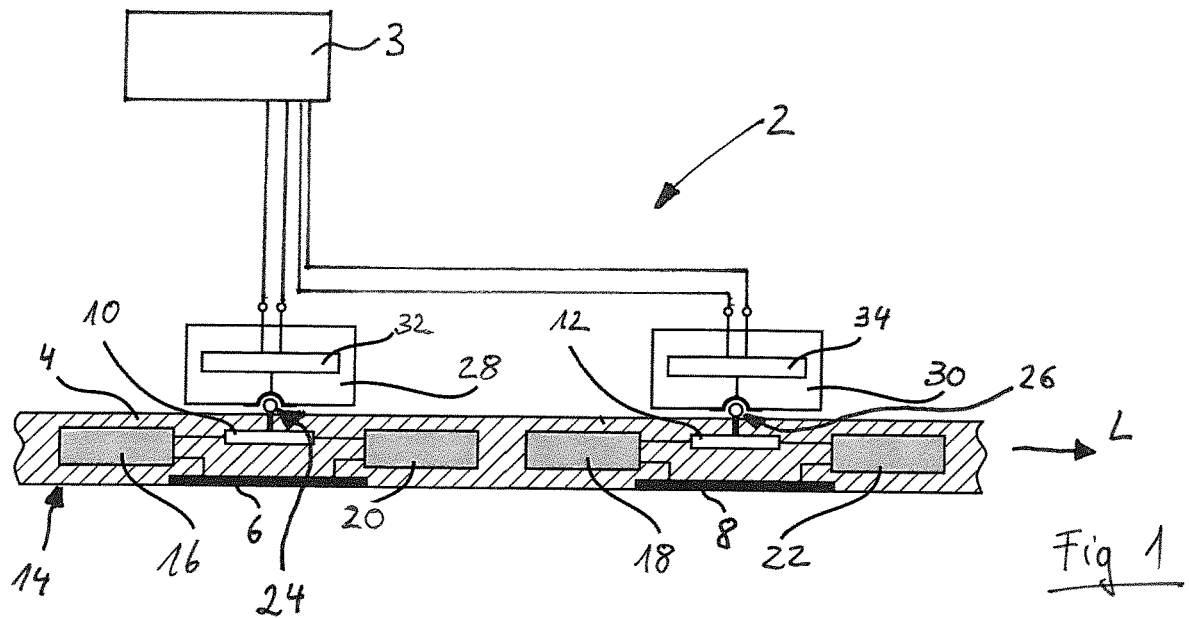
FIG. 1 is a schematic sectional view of the device according to the present invention.

Referring to the drawings, FIG. 1 shows the device 2 according to the present invention for an electrical impedance tomograph 3. The device 2 comprises for this an electrode carrier 4. It is preferably a so-called electrode belt. The electrode carrier 4 can consequently be placed like a belt around the body of a patient. To transmit the electrical signals necessary for the impedance tomography to the body or to pick up electrical signals, the device 2 comprises a first skin electrode 6 and a second skin electrode 8. The first and second skin electrodes 6, 8 are arranged on the electrode carrier 4 at mutually spaced locations from one another in the longitudinal direction L of the electrode carrier 4. If the electrode carrier 4 is bent in a ring-shaped manner, the skin electrodes 6, 8 are arranged radially on the inner side. The skin electrodes 6, 8 consequently come directly into contact with the patient's body and can thus guarantee the transmission of the desired signals. As is seen in FIG. 1, the skin electrodes 6, 8 may end continuously flush with an end face 14 of the electrode carrier 4.

It may happen in a situation that is critical for the patient that the impedance tomograph 3 and a defibrillator are used simultaneously. High voltage pulses are emitted by the defibrillator. To prevent the voltage pulses emitted by the defibrillator from damaging or even destroying the impedance tomograph 3, it proved to be advantageous to provide a first protective circuit 10 for the device 2. The protective circuit 10 is to be enclosed at least partly in the electrode carrier 4. It was, however, found in practice that it is advantageous if the protective circuit 10 as a whole or at least a first capacitor 16 of the first protective circuit 10 is enclosed in the electrode carrier 4. An embodiment in which the entire first protective circuit 10 with its corresponding first capacitor 16 is enclosed in the electrode carrier 4 is shown in FIG. 1.

To make it possible to place the electrode carrier 4 around the body of a patient, it is necessary for the electrode carrier 4 to have the most flexible possible configuration by at least a second protective circuit 12 being provided, which is enclosed at least partly in the electrode carrier 4. Analogously to the first protective circuit 10, the second protective circuit 12 may comprise a second capacitor 18. It should be mentioned at this point that the first capacitor 16 and the second capacitor 18 are always meant to be a capacitor each. Even though the first protective circuit 10 and the second protective circuit 12 may also have additional capacitors each, this is not absolutely necessary.

Moreover, provisions are made for the first protective circuit 10 to be electrically connected to the first skin electrode 6. The second protective electrode 12 is electrically connected to the second skin electrode 8. Each of the skin electrodes 6, 8 is preferably connected electrically directly to the capacitor 16, 18 of the respective electrically connected protective circuit 10, 12. The coupling of the first protective circuit 10 with the first skin electrode 6 and the coupling of the second protective circuit 12 with the second skin electrode 8 offer the advantage that the protection against electrical pulses of a defibrillator takes place close to the electrodes. Since a plurality of protective circuits 10, 12 are provided, they have a relatively small overall size each, so that the flexibility of the electrode carrier 4 is preserved even if the protective circuits 10, 12 are enclosed in the electrode carrier 4. To facilitate the flexibility of the electrode carrier 4 even more, it proved to be advantageous in practice to split the electrical capacitance provided for a protective circuit 10, 12 among a plurality of capacitors. It is thus advantageous, for example, if the first protective circuit 10 encloses the first capacitor 16 and an additional capacitor 20. The two capacitors 16, 20 can thus provide the capacitance desired for the first protective circuit 10. The second capacitor 18 and an additional capacitor 22 may correspondingly be provided for the second protective circuit 12. The desired capacitance is split in this case as well. With a plurality of capacitors 16, 20, 18, 22, each of the capacitors 16, 20, 18, 22 has a smaller overall size. This guarantees greater flexibility of the electrode carrier 4.

A corresponding terminal 24, 26 is provided for each of the protective circuits 10, 12. The first terminal 24 is connected to the first protective circuit 10. The second terminal 26 is connected to the second protective circuit 12. The terminals 24, 26 are used to connect the protective circuits 10, 12 to the impedance tomograph 3.

It proved to be advantageous in practice if a preprocessing unit is provided between the impedance tomograph 3 and the electrode carrier 4. A preprocessing unit 26, 30 is especially preferably associated with each of the skin electrodes 6, 8 and with each of the protective circuits 10, 12. Thus, the first protective circuit 10 can be connected to a first preprocessing unit 28. The second protective circuit 12 may be connected to a second preprocessing unit 30. The two preprocessing units 28, 30 are preferably connected to the impedance tomograph 3 by means of electrical lines. The signals detected by the skin electrodes 6, 8 can be subjected to preprocessing and/or at least partly analyzed with the preprocessing units 28, 30. The preprocessing units 28, 30 may be configured especially for transmitting, adapting and/or amplifying an electrical signal. To accomplish its respective purpose, each preprocessing unit 28, 30 may comprise an electronic unit 32, 34 with active and/or passive electrical components.

Figure 2:
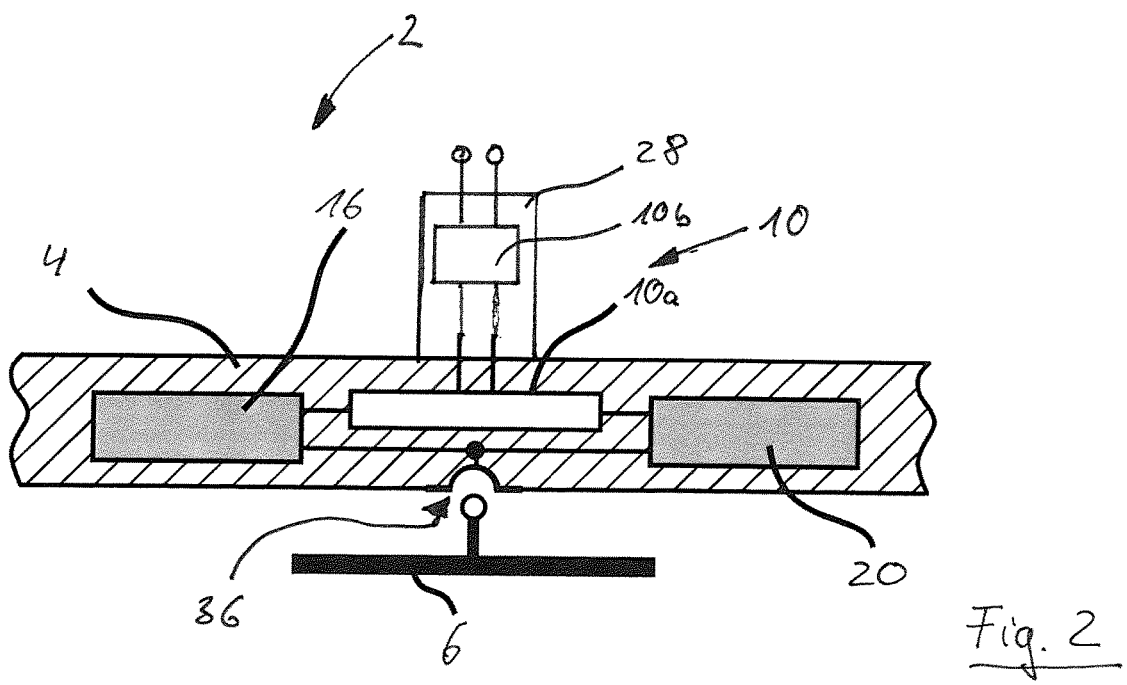
FIG. 2 is a schematic sectional view of a detail of the device according to the present invention.

FIG. 2 shows a detail of the device 2 according to the present invention, said detail containing the electrode carrier 4, the first skin electrode 6 and the first protective circuit 10. The first protective circuit 10 is electrically connected to the first skin electrode 6. When aspects related to the first skin electrode 6 and/or to the first protective circuit 10 will be explained below, they shall analogously apply to the second skin electrode 8 and to the second protective circuit 12.

The electrode carrier 4 has a receptacle 36 for the first skin electrode 6. The first skin electrode 6 can be inserted into this receptacle 36 and/or fastened by same. It is thus possible that the first skin electrode 6 is detachably fastened to the electrode carrier 4. A quick fastening is preferably formed between the first skin electrode 6 and the electrode carrier 4.

In addition, FIG. 2 shows that the protective circuit 10 has a multipart configuration. It has in this case a first protective circuit part 10a and a second protective circuit part 10b. The first protective circuit part 10a is fully enclosed in the electrode carrier 4. The second protective circuit part 10b is associated with the preprocessing unit 28. The two parts of the protective circuit 10 are connected by means of corresponding electrical lines. The first preprocessing unit 28 may be permanently or detachably fastened to the electrode carrier 4. Corresponding quick fastening devices may be provided in case of a detachable fastening of the first preprocessing unit 28. Due to the splitting of the first protective circuit 10, it is possible to utilize the space available for installation as optimally as possible. In addition, components of the protective circuit 10, which protect a user of the impedance tomograph 3 or a user of the defibrillator, may be integrated in the first protective circuit part 10a. Thus, the first protective circuit part 10a may have, for example, a high-voltage protection. Additional electrical components of the protective circuit 10 may thus be enclosed by the second protective circuit part 10b. Should the first preprocessing unit 28 be fastened detachably to the electrode carrier 4, the aforementioned user is protected against being inadvertently exposed to a high voltage pulse of the defibrillator.

Figure 3:
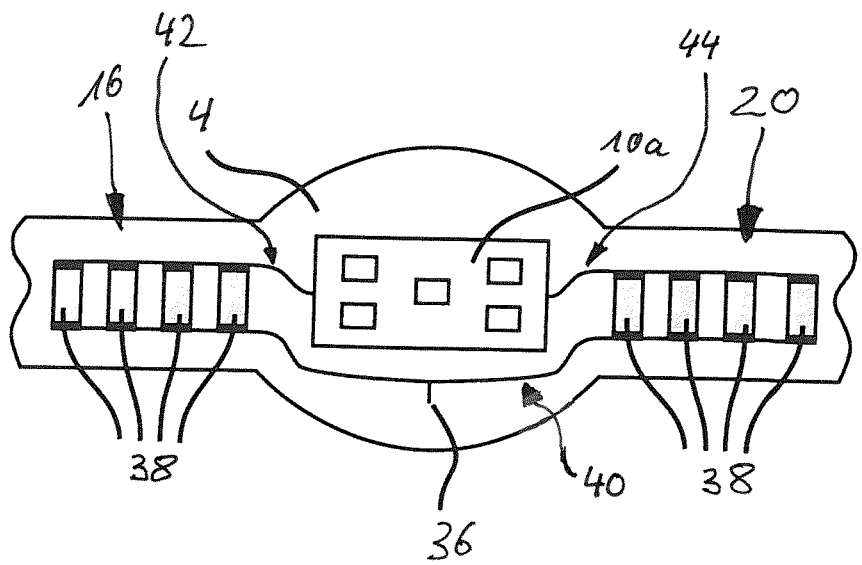
FIG. 3 is a schematic top view of a detail of the device according to the present invention.

FIG. 3 shows a schematic top view of the detail of device 2 from FIG. 2. It shows that the first capacitor 16 and the additional capacitor 20 are split each into a plurality of individual capacitors 38, which are configured each, for example, as SMD. The individual capacitors 38 may be arranged in parallel to one another in order to form the first capacitor 16 and the additional capacitor 20. One terminal each of each individual capacitor 38 is especially preferably connected to a common electrical connection line 40. The receptacle 36 is also connected to this connection line 40 in order to connect the first skin electrode 6 to same. The remaining terminals of the individual capacitors 38 of the first condenser 16 are connected by means of an additional connection line 42. This additional connection line 42 is connected to the rest of the first protective circuit part 10a and to the rest of the first protective circuit 10. An additional connection line 44, with which the other terminals of the individual capacitors 38, which terminals belong to the additional capacitor 20, are connected, is analogously provided for the additional capacitor 20. The additional connection line 44 is likewise connected to the rest of the first protective circuit part 10a and to the rest of the first protective circuit 10. It is possible with the configuration explained in connection with FIG. 3 that the electrode carrier 4 has a flexible configuration at least in the area between the skin electrodes 6, 8 in order make it possible for the electrode carrier 4 to be closely in contact with the body of the patient.

Figure 4:
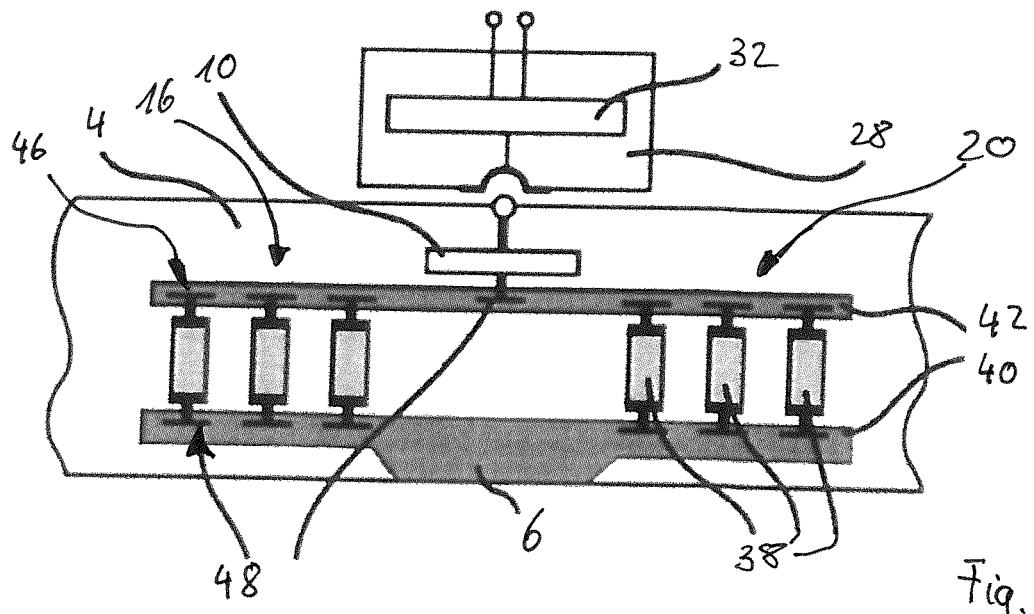
FIG. 4 is another schematic sectional view of a detail of the device according to the present invention.

FIG. 4 shows further aspects of the configuration of the device 2. Analogously to FIG. 2, it is noted here as well that the electrode carrier 4 with the first protective circuit 10 and with the first skin electrode 6 will be explained below, and the features and advantages mentioned shall also analogously apply to the second protective circuit 12 and to the second skin electrode 8.

It can be seen in FIG. 4 that the additional connection line 42 electrically connects a respective terminal 46 of each individual capacitor 38 of the first capacitor 16 and of the additional capacitor 20 to one another. The individual capacitors 38 are connected with their respective additional terminal 48 to a connection line 40. This connection line 40 is configured such that it forms the first skin electrode 6.

While specific embodiments of the invention have been shown and described in detail to illustrate the application of the principles of the invention, it will be understood that the invention may be embodied otherwise without departing from such principles.

The invention claimed is:

1. A device for an electrical impedance tomograph, the device comprising:
    an electrode carrier configured to be arranged around a body of a patient;
    a first skin electrode and a second skin electrode arranged on the electrode carrier at mutually spaced locations from one another in a longitudinal direction of the electrode carrier, the first and second electrodes being arranged on a radial inside of said electrode carrier when the electrode carrier is arranged around the body of the patient;
    a first protective circuit at least partly enclosed in the electrode carrier, the first protective circuit comprising a first capacitor;
    a second protective circuit at least partly enclosed in the electrode carrier, the second protective circuit comprising a second capacitor, wherein:
    the first protective circuit is electrically connected to the first skin electrode and arranged adjacent to the first skin electrode;
    the second protective circuit is electrically connected to the second skin electrode and arranged adjacent to the second skin electrode; and
    at least a respective inner part of the electrode carrier is formed by the first and second capacitor;
    wherein one of the protective circuits is arranged between the first and second skin electrodes in the longitudinal direction of the electrode carrier;
    at least one of the first and second capacitors are configured as a flexible capacitor.

2. A device in accordance with claim 1, wherein one of the protective circuits and one of the skin electrodes overlap each other in the longitudinal direction.

3. A device in accordance with claim 1, wherein the first and second protective circuits comprise an interface each to a control unit.

4. A device in accordance with claim 3, wherein the control unit is comprised by the impedance tomograph or is arranged on the electrode carrier.

5. A device in accordance with claim 1, wherein the first and second skin electrodes are detachably fastened to the electrode carrier or are integrated in the electrode carrier.

6. A device in accordance with claim 1, wherein:
    at least one of the first and second capacitors are configured as a surface mount device.

7. A device in accordance with claim 1, wherein:
    a dielectric of the at least one of the first and second capacitors is configured as a flexible foil.

8. A device in accordance with claim 1, wherein capacitor contact surfaces of each capacitor are configured as flexible foils.

9. A device in accordance with claim 1, wherein:
    the electrode carrier forms at least one part of each dielectric of at least one of the first and second capacitors.

10. A device in accordance with claim 1, wherein:
    said first and second protective circuits with their respective first and second capacitors are configured to at least partially block a defibrillation signal from a patient.

11. A device for an electrical impedance tomograph, the device comprising:
    an electrode carrier configured to be arranged around a body of a patient;
    a first skin electrode and a second skin electrode arranged on the electrode carrier at mutually spaced locations from one another in a longitudinal direction of the electrode carrier, the first and second electrodes being arranged on a radial inside of said electrode carrier when the electrode carrier is arranged around the body of the patient;
    a first protective circuit at least partly enclosed in the electrode carrier, the first protective circuit comprising a first capacitor;
    a second protective circuit at least partly enclosed in the electrode carrier, the second protective circuit comprising a second capacitor, wherein:
    the first protective circuit is electrically connected to the first skin electrode;
    the second protective circuit is electrically connected to the second skin electrode;
    the first and second protective circuits with their respective first and second capacitors are configured to block a defibrillation signal from a patient from damaging the electrical impedance tomograph;
    wherein one of the first and second capacitors is arranged between the first and second skin electrodes in the longitudinal direction of the electrode carrier;
    the first and second capacitors are configured as a flexible capacitor.

* * * * *